(12) United States Patent
Sartor

(10) Patent No.: US 10,973,543 B2
(45) Date of Patent: Apr. 13, 2021

(54) DUAL WALL TISSUE EXTRACTION BAG

(71) Applicant: Covidien LP, Mansfield, MA (US)

(72) Inventor: Joe Don Sartor, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 377 days.

(21) Appl. No.: 16/157,425

(22) Filed: Oct. 11, 2018

(65) Prior Publication Data

US 2019/0209194 A1 Jul. 11, 2019

Related U.S. Application Data

(60) Provisional application No. 62/615,621, filed on Jan. 10, 2018.

(51) Int. Cl.
| | | |
|---|---|---|
| *A61B 17/3205* | (2006.01) | |
| *A61B 17/32* | (2006.01) | |
| *A61B 17/34* | (2006.01) | |
| *A61B 17/00* | (2006.01) | |
| *A61B 90/00* | (2016.01) | |

(52) U.S. Cl.
CPC .... *A61B 17/3205* (2013.01); *A61B 17/00234* (2013.01); *A61B 17/32002* (2013.01); *A61B 17/3423* (2013.01); *A61B 2017/00287* (2013.01); *A61B 2017/00853* (2013.01); *A61B 2090/0801* (2016.02); *A61B 2090/0807* (2016.02)

(58) Field of Classification Search
CPC ........ A61B 17/00234; A61B 17/32002; A61B 17/3205; A61B 17/3423; A61B 17/32056; A61B 2017/00287; A61B 2017/00853; A61B 2017/320024; A61B 2017/0225; A61B 2017/320064; A61B 2090/0801; A61B 2090/0807; A61B 18/1482

See application file for complete search history.

(56) References Cited

U.S. PATENT DOCUMENTS

| | | |
|---|---|---|
| 30,471 A | 10/1860 | Dudley |
| 31,564 A | 5/1862 | Logan et al. |
| 156,477 A | 11/1874 | Bradford |
| 1,609,014 A | 11/1926 | Dowd |

(Continued)

FOREIGN PATENT DOCUMENTS

| | | |
|---|---|---|
| DE | 3542667 A1 | 6/1986 |
| DE | 8435489 U1 | 8/1986 |

(Continued)

OTHER PUBLICATIONS

European Search Report EP 12191639.9 dated Feb. 20, 2013.

(Continued)

*Primary Examiner* — Mohamed G Gabr

(57) ABSTRACT

The present disclosure is directed to extraction bags for use in removing tissue from the body of a patient, in embodiments, as part of a minimally invasive surgical procedure. The extraction bag includes at least an inner, permeable cut resistant layer and an outer impermeable layer. In embodiments, the extraction bag may include additional layers, such as a low friction layer on an inner surface of the inner, permeable cut resistant layer, and/or a metal cut resistant layer located between the inner, permeable cut resistant layer and the outer impermeable layer.

17 Claims, 2 Drawing Sheets

(56) References Cited

U.S. PATENT DOCUMENTS

| | | |
|---|---|---|
| 3,800,781 A | 4/1974 | Zalucki |
| 4,557,255 A | 12/1985 | Goodman |
| 4,611,594 A | 9/1986 | Grayhack et al. |
| 4,744,363 A | 5/1988 | Hasson |
| 4,790,812 A | 12/1988 | Hawkins, Jr. et al. |
| 4,852,586 A | 8/1989 | Haines |
| 4,927,427 A | 5/1990 | Kriauciunas et al. |
| 4,977,903 A | 12/1990 | Haines |
| 4,991,593 A | 2/1991 | LeVahn |
| 4,997,435 A | 3/1991 | Demeter |
| 5,037,379 A * | 8/1991 | Clayman .......... A61B 17/00234 600/37 |
| 5,074,867 A | 12/1991 | Wilk |
| 5,084,054 A | 1/1992 | Bencini et al. |
| 5,143,082 A | 9/1992 | Kindberg et al. |
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,190,561 A | 3/1993 | Graber |
| 5,192,284 A | 3/1993 | Pleatman |
| 5,192,286 A | 3/1993 | Phan et al. |
| 5,201,740 A | 4/1993 | Nakao et al. |
| 5,215,521 A | 6/1993 | Cochran et al. |
| 5,224,930 A | 7/1993 | Spaeth et al. |
| 5,234,439 A | 8/1993 | Wilk et al. |
| 5,279,539 A | 1/1994 | Bohan et al. |
| 5,312,416 A | 5/1994 | Spaeth et al. |
| 5,320,627 A | 6/1994 | Sorensen et al. |
| 5,330,483 A | 7/1994 | Heaven et al. |
| 5,336,227 A | 8/1994 | Nakao et al. |
| 5,337,754 A | 8/1994 | Heaven et al. |
| 5,341,815 A | 8/1994 | Cofone et al. |
| 5,352,184 A | 10/1994 | Goldberg et al. |
| 5,354,303 A | 10/1994 | Spaeth et al. |
| 5,368,545 A | 11/1994 | Schaller et al. |
| 5,368,597 A | 11/1994 | Pagedas |
| 5,370,647 A | 12/1994 | Graber et al. |
| 5,443,472 A | 8/1995 | Li |
| 5,465,731 A | 11/1995 | Bell et al. |
| 5,480,404 A | 1/1996 | Kammerer et al. |
| 5,486,182 A | 1/1996 | Nakao et al. |
| 5,486,183 A | 1/1996 | Middleman et al. |
| 5,499,988 A | 3/1996 | Espiner et al. |
| 5,524,633 A | 6/1996 | Heaven et al. |
| 5,535,759 A | 7/1996 | Wilk |
| 5,611,803 A | 3/1997 | Heaven et al. |
| 5,618,296 A | 4/1997 | Sorensen et al. |
| 5,630,822 A | 5/1997 | Hermann et al. |
| 5,642,282 A | 6/1997 | Sonehara |
| 5,643,282 A | 7/1997 | Kieturakis |
| 5,643,283 A | 7/1997 | Younker |
| 5,645,083 A | 7/1997 | Essig et al. |
| 5,647,372 A | 7/1997 | Tovey et al. |
| 5,649,902 A | 7/1997 | Yoon |
| 5,658,296 A | 8/1997 | Bates et al. |
| 5,679,423 A | 10/1997 | Shah |
| 5,681,324 A | 10/1997 | Kammerer et al. |
| 5,720,754 A | 2/1998 | Middleman et al. |
| 5,735,289 A | 4/1998 | Pfeffer et al. |
| 5,741,271 A | 4/1998 | Nakao et al. |
| 5,755,724 A | 5/1998 | Yoon |
| 5,759,187 A | 6/1998 | Nakao et al. |
| 5,769,794 A | 6/1998 | Conlan et al. |
| 5,782,840 A | 7/1998 | Nakao |
| 5,785,677 A | 7/1998 | Auweiler |
| 5,788,709 A | 8/1998 | Riek et al. |
| 5,792,145 A | 8/1998 | Bates et al. |
| 5,814,044 A | 9/1998 | Hooven |
| 5,829,440 A | 11/1998 | Broad, Jr. |
| 5,836,953 A | 11/1998 | Yoon |
| 5,853,374 A | 12/1998 | Hart et al. |
| 5,895,392 A | 4/1999 | Riek et al. |
| 5,904,690 A | 5/1999 | Middleman et al. |
| 5,906,621 A | 5/1999 | Secrest et al. |
| 5,908,429 A | 6/1999 | Yoon |
| 5,957,884 A | 9/1999 | Hooven |
| 5,971,995 A | 10/1999 | Rousseau |
| 5,980,544 A | 11/1999 | Vaitekunas |
| 5,997,547 A | 12/1999 | Nakao et al. |
| 6,004,330 A | 12/1999 | Middleman et al. |
| 6,007,512 A | 12/1999 | Hooven |
| 6,007,546 A | 12/1999 | Snow et al. |
| 6,019,770 A | 2/2000 | Christoudias |
| 6,036,681 A | 3/2000 | Hooven |
| 6,059,793 A | 5/2000 | Pagedas |
| 6,123,701 A | 9/2000 | Nezhat |
| 6,152,932 A | 11/2000 | Ternstrom |
| 6,156,055 A | 12/2000 | Ravenscroft |
| 6,162,235 A | 12/2000 | Vaitekunas |
| 6,165,121 A | 12/2000 | Alferness |
| 6,168,603 B1 | 1/2001 | Leslie et al. |
| 6,206,889 B1 | 3/2001 | Bennardo |
| 6,228,095 B1 | 5/2001 | Dennis |
| 6,258,102 B1 | 7/2001 | Pagedas |
| 6,264,663 B1 | 7/2001 | Cano |
| 6,270,505 B1 | 8/2001 | Yoshida et al. |
| 6,277,083 B1 | 8/2001 | Eggers et al. |
| 6,280,450 B1 | 8/2001 | McGuckin, Jr. |
| 6,344,026 B1 | 2/2002 | Burbank et al. |
| 6,348,056 B1 | 2/2002 | Bates et al. |
| 6,350,266 B1 | 2/2002 | White et al. |
| 6,350,267 B1 | 2/2002 | Stefanchik |
| 6,368,328 B1 | 4/2002 | Chu et al. |
| 6,383,195 B1 | 5/2002 | Richard |
| 6,383,196 B1 | 5/2002 | Leslie et al. |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,471,659 B2 | 10/2002 | Eggers et al. |
| 6,506,166 B1 | 1/2003 | Hendler et al. |
| 6,508,773 B2 | 1/2003 | Burbank et al. |
| 6,537,273 B1 | 3/2003 | Sosiak et al. |
| 6,547,310 B2 | 4/2003 | Myers |
| 6,589,252 B2 | 7/2003 | McGuckin, Jr. |
| 6,752,811 B2 | 6/2004 | Chu et al. |
| 6,755,779 B2 | 6/2004 | Vanden Hoek et al. |
| 6,780,193 B2 | 8/2004 | Leslie et al. |
| 6,805,699 B2 | 10/2004 | Shimm |
| 6,840,948 B2 | 1/2005 | Albrecht et al. |
| 6,872,211 B2 | 3/2005 | White et al. |
| 6,887,255 B2 | 5/2005 | Shimm |
| 6,958,069 B2 | 10/2005 | Shipp et al. |
| 6,971,988 B2 | 12/2005 | Orban, III |
| 6,994,696 B2 | 2/2006 | Suga |
| 7,014,648 B2 | 3/2006 | Ambrisco et al. |
| 7,018,373 B2 | 3/2006 | Suzuki |
| 7,052,454 B2 | 5/2006 | Taylor |
| 7,052,501 B2 | 5/2006 | McGuckin, Jr. |
| 7,090,637 B2 | 8/2006 | Danitz et al. |
| 7,115,125 B2 | 10/2006 | Nakao et al. |
| 7,270,663 B2 | 9/2007 | Nakao |
| 7,273,488 B2 | 9/2007 | Nakamura et al. |
| 7,410,491 B2 | 8/2008 | Hopkins et al. |
| 7,547,310 B2 | 6/2009 | Whitfield |
| 7,618,437 B2 | 11/2009 | Nakao |
| 7,670,346 B2 | 3/2010 | Whitfield |
| 7,722,626 B2 | 5/2010 | Middleman et al. |
| 7,762,959 B2 | 7/2010 | Bilsbury |
| 7,785,251 B2 | 8/2010 | Wilk |
| 7,819,121 B2 | 10/2010 | Amer |
| 7,837,612 B2 | 11/2010 | Gill et al. |
| RE42,050 E | 1/2011 | Richard |
| 7,892,242 B2 | 2/2011 | Goldstein |
| 8,016,771 B2 | 9/2011 | Orban, III |
| 8,057,485 B2 | 11/2011 | Hollis et al. |
| 8,075,567 B2 | 12/2011 | Taylor et al. |
| 8,097,001 B2 | 1/2012 | Nakao |
| 8,152,820 B2 | 4/2012 | Mohamed et al. |
| 8,172,772 B2 | 5/2012 | Zwolinski et al. |
| 8,206,401 B2 | 6/2012 | Nakao |

(56) References Cited

U.S. PATENT DOCUMENTS

| | | |
|---|---|---|
| 8,337,510 B2 | 12/2012 | Rieber et al. |
| 8,343,031 B2 | 1/2013 | Gertner |
| 8,348,827 B2 | 1/2013 | Zwolinski |
| 8,388,630 B2 | 3/2013 | Teague et al. |
| 8,409,112 B2 | 4/2013 | Wynne et al. |
| 8,409,216 B2 | 4/2013 | Parihar et al. |
| 8,409,217 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |
| 8,430,826 B2 | 4/2013 | Uznanski et al. |
| 8,435,237 B2 | 5/2013 | Bahney |
| 8,444,655 B2 | 5/2013 | Parihar et al. |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,696,683 B2 | 4/2014 | LeVert |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,906,036 B2 | 12/2014 | Farascioni |
| 8,956,370 B2 | 2/2015 | Taylor et al. |
| 8,968,329 B2 | 3/2015 | Cabrera |
| 2002/0068943 A1 | 6/2002 | Chu et al. |
| 2002/0082516 A1 | 6/2002 | Stefanchik |
| 2003/0073970 A1 | 4/2003 | Suga |
| 2003/0100909 A1 | 5/2003 | Suzuki |
| 2003/0100919 A1 | 5/2003 | Hopkins et al. |
| 2003/0199915 A1 | 10/2003 | Shimm |
| 2003/0216773 A1 | 11/2003 | Shimm |
| 2004/0097960 A1 | 5/2004 | Terachi et al. |
| 2004/0138587 A1 | 7/2004 | Lyons |
| 2005/0085808 A1 | 4/2005 | Nakao |
| 2005/0165411 A1 | 7/2005 | Orban |
| 2005/0267492 A1 | 12/2005 | Poncet et al. |
| 2006/0030750 A1 | 2/2006 | Amer |
| 2006/0052799 A1 | 3/2006 | Middleman et al. |
| 2006/0058776 A1 | 3/2006 | Bilsbury |
| 2006/0169287 A1 | 8/2006 | Harrison et al. |
| 2006/0200169 A1 | 9/2006 | Sniffin |
| 2006/0200170 A1 | 9/2006 | Aranyi |
| 2006/0229639 A1 | 10/2006 | Whitfield |
| 2006/0229640 A1 | 10/2006 | Whitfield |
| 2007/0016224 A1 | 1/2007 | Nakao |
| 2007/0016225 A1 | 1/2007 | Nakao |
| 2007/0073251 A1 | 3/2007 | Zhou et al. |
| 2007/0088370 A1 | 4/2007 | Kahle et al. |
| 2007/0135780 A1* | 6/2007 | Pagedas ............. A61B 17/3207 604/327 |
| 2007/0135781 A1 | 6/2007 | Hart |
| 2007/0186935 A1 | 8/2007 | Wang et al. |
| 2008/0188766 A1 | 8/2008 | Gertner |
| 2008/0221587 A1 | 9/2008 | Schwartz |
| 2008/0221588 A1 | 9/2008 | Hollis et al. |
| 2008/0234696 A1 | 9/2008 | Taylor et al. |
| 2008/0300621 A1 | 12/2008 | Hopkins et al. |
| 2008/0312496 A1 | 12/2008 | Zwolinski |
| 2009/0043315 A1 | 2/2009 | Moon |
| 2009/0082779 A1 | 3/2009 | Nakao |
| 2009/0182292 A1 | 7/2009 | Egle et al. |
| 2009/0192510 A1 | 7/2009 | Bahney |
| 2009/0240238 A1 | 9/2009 | Grodrian et al. |
| 2010/0000471 A1 | 1/2010 | Hibbard |
| 2010/0152746 A1 | 6/2010 | Ceniccola et al. |
| 2011/0087235 A1 | 4/2011 | Taylor et al. |
| 2011/0184311 A1 | 7/2011 | Parihar et al. |
| 2011/0184434 A1 | 7/2011 | Parihar et al. |
| 2011/0184435 A1 | 7/2011 | Parihar et al. |
| 2011/0184436 A1 | 7/2011 | Shelton, IV et al. |
| 2011/0190779 A1* | 8/2011 | Gell ................. A61B 17/00234 606/114 |
| 2011/0190781 A1 | 8/2011 | Collier et al. |
| 2011/0190782 A1 | 8/2011 | Fleming et al. |
| 2011/0264091 A1 | 10/2011 | Koppleman et al. |
| 2011/0299799 A1 | 12/2011 | Towe |
| 2012/0046667 A1 | 2/2012 | Cherry et al. |
| 2012/0083795 A1 | 4/2012 | Fleming et al. |
| 2012/0083796 A1 | 4/2012 | Grover et al. |
| 2012/0203241 A1 | 8/2012 | Williamson, IV |
| 2013/0023895 A1 | 1/2013 | Saleh |
| 2013/0103042 A1 | 4/2013 | Davis |
| 2013/0116592 A1 | 5/2013 | Whitfield |
| 2013/0190773 A1 | 7/2013 | Carlson |
| 2013/0218170 A1 | 8/2013 | Uznanski et al. |
| 2013/0245636 A1 | 9/2013 | Jansen |
| 2013/0274758 A1 | 10/2013 | Young et al. |
| 2013/0325025 A1 | 12/2013 | Hathaway et al. |
| 2014/0046337 A1 | 2/2014 | O'Prey et al. |
| 2014/0058403 A1 | 2/2014 | Menn et al. |
| 2014/0180303 A1 | 6/2014 | Duncan et al. |
| 2014/0222016 A1 | 8/2014 | Grover et al. |
| 2014/0236110 A1 | 8/2014 | Taylor et al. |
| 2014/0243865 A1 | 8/2014 | Swayze et al. |
| 2014/0249541 A1 | 9/2014 | Kahle et al. |
| 2014/0276913 A1 | 9/2014 | Tah et al. |
| 2014/0303640 A1 | 10/2014 | Davis et al. |
| 2014/0309656 A1 | 10/2014 | Gal et al. |
| 2014/0330285 A1 | 11/2014 | Rosenblatt et al. |
| 2014/0350567 A1 | 11/2014 | Schmitz et al. |
| 2014/0371759 A1 | 12/2014 | Hartoumbekis |
| 2014/0371760 A1 | 12/2014 | Menn |
| 2015/0018837 A1 | 1/2015 | Sartor et al. |
| 2015/0045808 A1 | 2/2015 | Farascioni |

FOREIGN PATENT DOCUMENTS

| | | |
|---|---|---|
| DE | 4204210 A1 | 8/1992 |
| DE | 19624826 A1 | 1/1998 |
| EP | 0947166 A2 | 10/1999 |
| EP | 1685802 A1 | 8/2006 |
| EP | 1707126 A1 | 10/2006 |
| EP | 2005900 A2 | 12/2008 |
| EP | 2184014 A2 | 5/2010 |
| EP | 2436313 A2 | 4/2012 |
| EP | 2474270 A2 | 7/2012 |
| FR | 1272412 A | 9/1961 |
| GB | 246009 A | 1/1926 |
| WO | 9315675 A1 | 8/1993 |
| WO | 9509666 A1 | 4/1995 |
| WO | 0135831 A1 | 5/2001 |
| WO | 2004002334 A1 | 1/2004 |
| WO | 2004112571 A2 | 12/2004 |
| WO | 2005112783 A1 | 12/2005 |
| WO | 2006110733 | 10/2006 |
| WO | 2007048078 A1 | 4/2007 |
| WO | 2007048085 A2 | 4/2007 |
| WO | 2008114234 A2 | 9/2008 |
| WO | 2009149146 A1 | 12/2009 |
| WO | 2011090862 A2 | 7/2011 |

OTHER PUBLICATIONS

European Search Report EP 11250837.9 dated Sep. 10, 2013.
European Search Report EP 11250838.7 dated Sep. 10, 2013.
European Search Report EP 13170118.7 dated Dec. 5, 2013.
European Search Report EP 12165852 dated Jun. 20, 2012.
http://www.biomaterials.org/week/bio17.cfm, definition and examples of hydrogels.
European Search Report EP 12150271 dated Jan. 14, 2013.
European Search Report EP 12193450 dated Feb. 27, 2013.
European Search Report EP 12189517.1 dated Mar. 6, 2013.
European Search Report EP 12158873 dated Jul. 19, 2012.
European Search Report EP 11250836 dated Sep. 12, 2013.

* cited by examiner

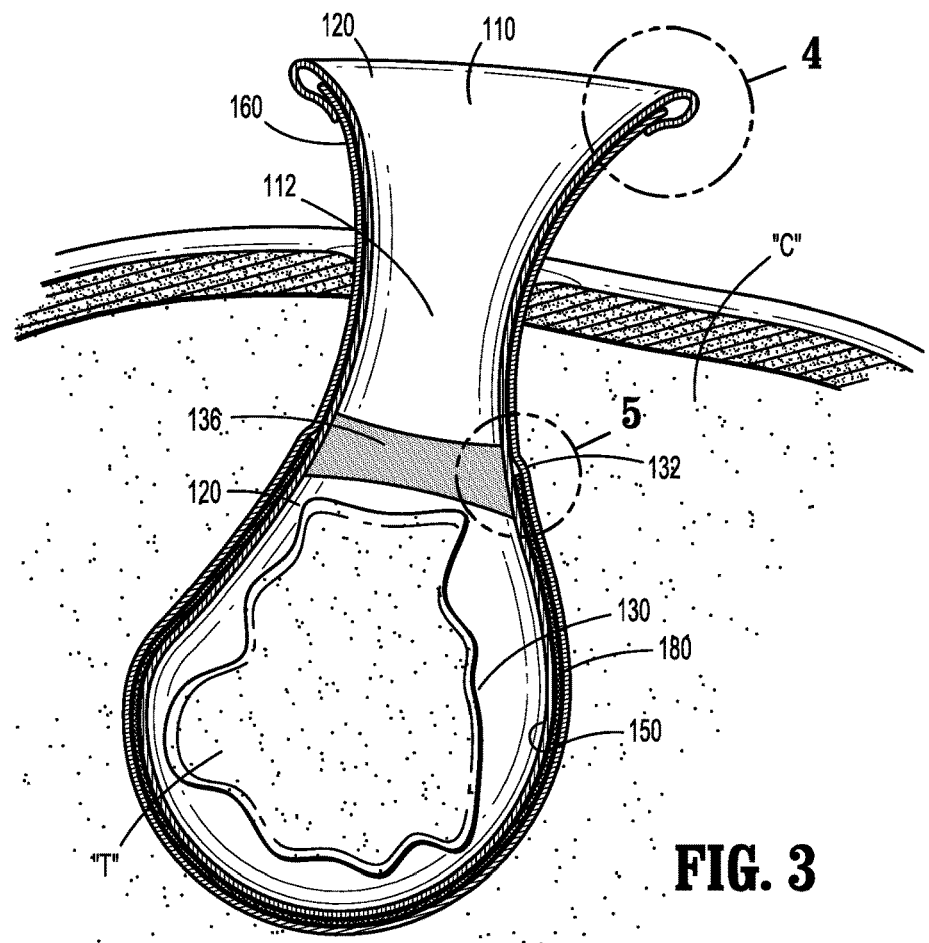
FIG. 3
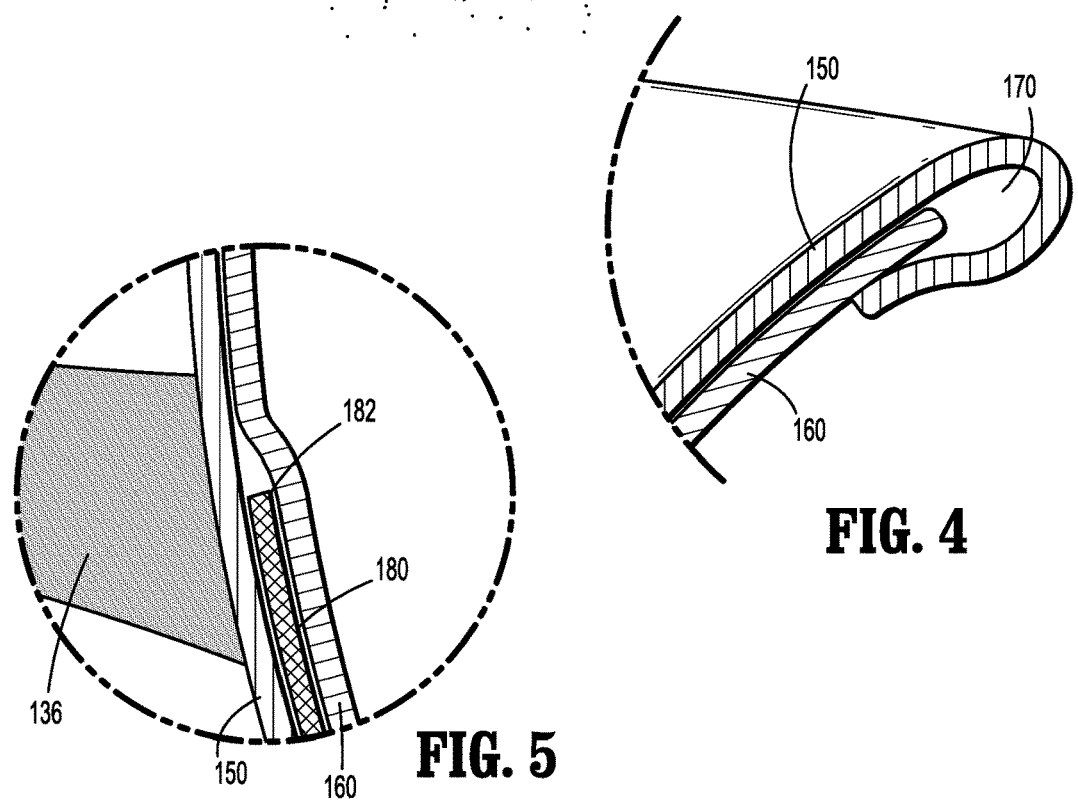
FIG. 4
FIG. 5

DUAL WALL TISSUE EXTRACTION BAG

CROSS-REFERENCE TO RELATED APPLICATION

This application claims the benefit of and priority to U.S. Provisional Patent Application No. 62/615,621 filed Jan. 10, 2018, the entire disclosure of which is incorporated by reference herein.

TECHNICAL FIELD

The present disclosure relates to an extraction bag for collecting body tissue(s) and/or body fluid(s) during minimally invasive surgical procedures.

BACKGROUND

Minimally invasive surgery, such as endoscopic surgery, reduces the invasiveness of surgical procedures. Endoscopic surgery involves surgery through body walls, for example, viewing and/or operating on the ovaries, uterus, gall bladder, bowels, kidneys, appendix, etc. There are many common endoscopic surgical procedures, including arthroscopy, laparoscopy, gastroentroscopy and laryngobronchoscopy, just to name a few. In these procedures, trocars are utilized for creating incisions through which the endoscopic surgery is performed. Trocar tubes or cannula devices are extended into and left in place in the abdominal wall to provide access for endoscopic surgical tools. A camera or endoscope is inserted through a trocar tube to permit the visual inspection and magnification of the body cavity. The surgeon can then perform diagnostic and/or therapeutic procedures at the surgical site with the aid of specialized instrumentation, such as forceps, cutters, applicators, and the like, which are designed to fit through additional cannulas.

When removing tumor tissue from the abdominal space, it is important that the tumor tissue does not come into contact with healthy or uninvolved tissue, so as in this way to avoid metastasis and thus avoid harming the patient. Minimally invasive surgical procedures, however, may be limited where large size tumors or large masses of tissue have to be removed from a body cavity. If tumor tissue or tissue parts have to be removed, they may be introduced into an "extraction bag" at the site where the tumor or diseased tissue has been detached from the surrounding tissue, after which the extraction bag is withdrawn from the body, normally through a trocar or similar device, thereby minimizing contact of the diseased tissue with healthy tissue.

In some instances, depending upon the volume of tissue being removed from the body, the tissue within the extraction bag must be broken up prior to removal from the body to allow for the extraction bag and its contents to pass through the opening used to conduct the endoscopic procedure.

Improved extraction bags for removal of tissue remain desirable.

SUMMARY

The present disclosure is directed to extraction bags for use in minimally invasive surgery.

In embodiments, an extraction bag of the present disclosure includes a body defining a cavity and having an open end in communication with the cavity, the body formed of an inner, permeable cut resistant layer defining the cavity and an outer impermeable layer, at least a portion of a peripheral border of the inner, permeable cut resistant layer affixed to at least a portion of a peripheral border of the outer impermeable layer, thereby forming a fluid collection space between the inner, permeable cut resistant layer and the outer impermeable layer.

The inner, permeable cut resistant layer of the extraction bag may be formed of suitable materials such as liquid crystal polymer fibers, para-aramid fibers, ultrahigh molecular weight polyethyelene fibers, polytetrafluoroethylene fibers, polyurethanes, polyethylenes, block copolyetheramides, polymers of p-phenylene-2,6-benzobisoxazole, and combinations thereof.

The outer impermeable layer of the extraction bag may be formed of suitable materials such as polyethylene, polyurethanes, polyesters, polyethylene terephthalate, thermoplastic elastomers, thermoplastic vulcanizates, silicones, natural rubbers, styrene-butadiene-styrene block copolymers, and combinations thereof.

In some embodiments, the peripheral border of the inner, permeable cut resistant layer of the extraction bag may be affixed to the peripheral border of the outer impermeable layer by adhesive bonding, welding, heat laminating, heat-sealing, stitching, or combinations thereof.

In embodiments, the extraction bag possesses a cuff encompassing the open end, the cuff formed by folding a proximal portion of the inner, permeable cut resistant layer over a proximal portion of the outer impermeable layer and affixing the proximal portion of the inner, permeable cut resistant layer to an outer surface of the proximal portion of the outer impermeable layer of the body, thereby forming a channel within the cuff. In some embodiments, a drawstring may be within the channel within the cuff.

In some embodiments, the extraction bag also includes a low friction layer on an inner surface of the inner, permeable cut resistant layer. Where present, the low friction layer includes a material such as silicones, fluoropolymers and copolymers thereof, and combinations thereof.

In other embodiments, the extraction bag includes a metal cut resistant layer between the inner, permeable cut resistant layer and the outer impermeable layer. Where present, the metal cut resistant layer may be formed of a material such as stainless steel wires, tungsten, steel fiber yarns, and combinations thereof. In some embodiments, the metal cut resistant layer has an end spaced from the open end of the body and the extraction bag has an indicator designating the end of the metal cut resistant layer.

Alternate extraction bags of the present disclosure include a body defining a cavity and having an open end in communication with the cavity, the body formed of an inner, permeable cut resistant layer defining the cavity, an outer impermeable layer, and a metal cut resistant layer between the inner, permeable cut resistant layer and the outer impermeable layer.

In embodiments, the inner, permeable cut resistant layer may be formed of a material such as liquid crystal polymer fibers, para-aramid fibers, ultrahigh molecular weight polyethyelene fibers, polytetrafluoroethylene fibers, polyurethanes, polyethylenes, block copolyetheramides, polymers of p-phenylene-2,6-benzobisoxazole, and combinations thereof.

The outer impermeable layer may be formed of a material such as polyethylene, polyurethanes, polyesters, polyethylene terephthalate, thermoplastic elastomers, thermoplastic vulcanizates, silicones, natural rubbers, styrene-butadiene-styrene block copolymers, and combinations thereof.

The metal cut resistant layer may be formed of a material such as stainless steel wires, tungsten, steel fiber yarns, and combinations thereof.

In some embodiments, the extraction bag also includes a cuff encompassing the open end, the cuff formed by folding a proximal portion of the inner, permeable cut resistant layer over a proximal portion of the outer impermeable layer and affixing the proximal portion of the inner, permeable cut resistant layer to an outer surface of the proximal portion of the outer impermeable layer of the body, thereby forming a channel within the cuff. In other embodiments, a drawstring may be within the channel.

In embodiments, the extraction bag includes a low friction layer on an inner surface of the inner, permeable cut resistant layer. Where present, the low friction layer includes a material such as silicones, fluoropolymers and copolymers thereof, and combinations thereof.

In some embodiments, the metal cut resistant layer of the extraction bag has an end spaced from the open end of the body and the extraction bag has an indicator designating the end of the metal cut resistant layer.

BRIEF DESCRIPTION OF THE DRAWINGS

Various embodiments are described herein with reference to the drawings wherein:

FIG. 3 is a side cross-sectional view of an alternative extraction bag of the present disclosure positioned within a body cavity of a patient;

FIG. 4 is an enlarged view of the indicated area of detail shown in FIG. 3; and FIG. 5 is an enlarged view of the indicated area of detail shown in FIG. 3.

DETAILED DESCRIPTION

Figure 1:
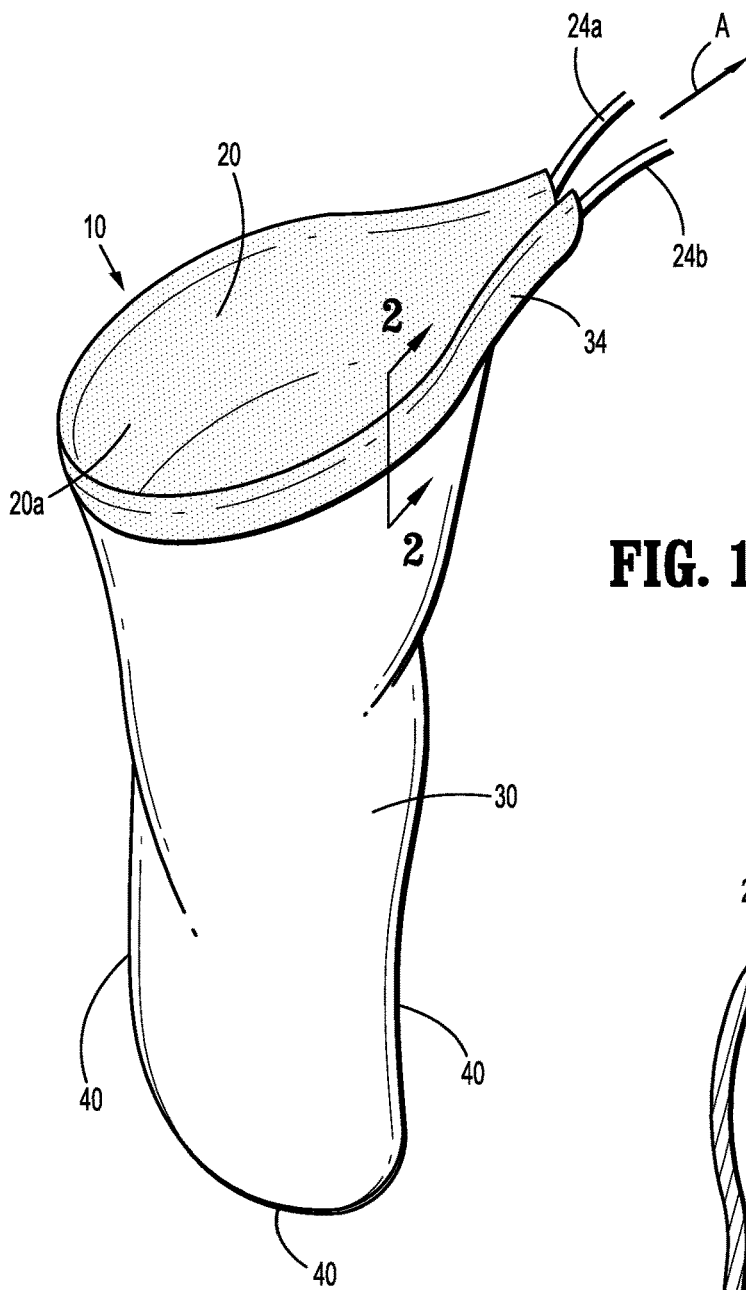
FIG. 1 is a perspective view of an extraction bag of the present disclosure.

As used herein, the term distal refers to the portion of the extraction bag of the present disclosure which is farthest from the user, while the term proximal refers to that portion of the extraction bag of the present disclosure which is closest to the user.

The present disclosure provides extraction bags suitable for use in any procedure where access to the interior of the body is limited to one or more relatively small incisions, with or without the use of a cannula or other access port, as in minimally invasive procedures. As used herein with reference to the present disclosure, minimally invasive surgical procedures encompass laparoscopic procedures and endoscopic procedures, and refer to procedures utilizing scopes or similar devices having relatively narrow operating portions for insertion into a cannula or a small incision in the skin.

The aspects of the present disclosure may be modified for use with various methods for retrieving tissue during minimally invasive procedures. Examples of minimally invasive procedures include, for example, cholecystectomies, appendectomies, nephrectomies, colectomies, splenectomies, and the like.

Extraction bags of the present disclosure are made of flexible and durable materials. The extraction bags include at least two layers, are cut resistant, and capable of allowing a clinician to introduce cutting devices into the extraction bag to reduce the size of tissue therein, thereby facilitating removal of the extraction bag from the body. Materials used to form the extraction bags are antistatic, pyrogen-free, non-toxic and sterilizable.

Extraction bags of the present disclosure include an inner, permeable cut resistant layer and an outer impermeable or fluid proof layer. Suitable materials for use as the inner, permeable cut resistant layer include various fabrics formed of, in embodiments, polymeric materials. Exemplary polymeric materials include, in embodiments, liquid crystal polymer (LCP) fibers, including those commercially available as VECTRAN® fibers (from Swicofil), para-aramid fibers, including those commercially available as KEVLAR® fibers (from Du Pont), ultrahigh molecular weight polyethyelene (UHMWPE), including those commercially available as SPECTRA® fibers (from Honeywell), polytetrafluoroethylene (PTFE) fibers, polyurethanes, polyethylenes, PEBAX® block copolyetheramides, fibers formed of polymers of p-phenylene-2,6-benzobisoxazole (PBO), including those commercially available as ZYLON® fibers (from Toyobo), combinations thereof, or any of various other suitable materials within the purview of those skilled in the art.

The outer impermeable layer of embodiments of extraction bags of the present disclosure is fluid proof and constructed of a film or coated fabric. Suitable materials for forming the outer impermeable layer include, in embodiments polyethylene, polyurethanes, polyesters, including polyethylene terephthalate (PET), thermoplastic elastomers, including thermoplastic vulcanizates, for example those sold as SANTOPRENE™ TPV (a vulcanized ethylene propylene diene monomer (EPDM) rubber in a thermoplastic matrix of polypropylene (PP)), silicones, natural rubbers, styrene-butadiene-styrene (SBS) block copolymers, including those commercially available as KRATON™ SBS (from Kraton Corporation), combinations thereof, or any of various other suitable materials within the purview of those skilled in the art.

The inner, permeable cut resistant layer and outer impermeable layer are joined at their periphery, but are not laminated together. If the two were layers were laminated together and/or one layer coated on the other, the binding of the outer impermeable layer to the inner, permeable cut resistant layer would reduce the mobility/elasticity of the inner, permeable cut resistant layer, and thus reduce its cut resistance. Accordingly, by only joining the layers at the periphery, and not laminating the two, the outer impermeable layer does not adversely impact the mobility/elasticity of the inner, permeable cut resistant layer, and thus does not adversely affect its cut resistance.

In embodiments, the inner, permeable cut resistant layer is permeable and defines a fluid collection space or cavity with the outer impermeable layer. In use, prior to removal of the extraction bag from the body, in order to reduce the volume of tissue/fluids within the extraction bag, the extraction bag may be compressed. When the extraction bag is compressed, tissue within the extraction bag is also compressed to force fluid from inside the extraction bag into the fluid collection space between the inner, permeable cut resistant layer and outer impermeable layer. A vacuum source or some other device for removing fluid from the fluid collection space may be introduced into the fluid collection space between the inner, permeable cut resistant layer and outer impermeable layer, thus reducing the volume of the extraction bag for removal from the body. In embodiments, the welding at the periphery of the inner, permeable cut resistant layer and the outer impermeable layer to join the two layers may be discontinuous, leaving at least a gap at a portion of the weld. The gap may be dimensioned to permit access to the space between the inner, permeable cut resistant layer and outer impermeable layer by the vacuum source or other device to remove fluids from the space.

The inner, permeable cut resistant layer and outer impermeable layer may be joined at the periphery by methods within the purview of those skilled in the art, including, but not limited to, using adhesives bonding, welding, heat-sealing, combinations thereof, and the like.

In embodiments, additional optional layers may be included in fabricating an extraction bag of the present disclosure. For example, in some embodiments the inner, permeable cut resistant layer may possess a low friction layer on its inner surface, to assist in the introduction of tissue into the extraction bag. Such low friction layers may be formed of, in embodiments, silicones that become slippery when wet, fluoropolymers and copolymers thereof, such as PTFE (including those commercially available as TEFLON polytetrafluoroethylene (from DuPont)), combinations thereof, and the like. These low friction layers may be applied as a coating to the inner surface of the inner, permeable cut resistant layer. In other embodiments, the low friction layer may be a separate layer joined to the inner, permeable cut resistant layer at its periphery, or could be laminated to the inner, permeable cut resistant layer, as long as it does not reduce the mobility/elasticity of the inner, permeable cut resistant layer, and thus reduce its cut resistance.

In other embodiments, an additional cut resistant layer, referred to in embodiments as a metal cut resistant layer, may be placed between the inner, permeable cut resistant layer and outer impermeable layer of the extraction bag. Suitable materials for forming the metal cut resistant layer include, for example, stainless steel wires, tungsten, steel fiber yarns, and combinations thereof, and the like. In embodiments, the metal cut resistant layer may be in the form of a mesh.

The metal cut resistant layer may be bound to the inner, permeable cut resistant layer or the outer impermeable layer at the periphery adjacent what will be the distal portion of the extraction bag, but not bound at what will be the open proximal end of the extraction bag. Instead, the proximal portion of the metal cut resistant layer will be bound to the inner, permeable cut resistant layer, the outer impermeable layer, or both, at a distance distal from the proximal portions of the inner, permeable cut resistant layer and outer impermeable layer. For an extraction bag possessing this configuration, the metal cut resistant layer extends from the distal closed end of the extraction bag towards the proximal open end of the extraction bag, but is not coterminous with the inner, permeable cut resistant layer and the outer impermeable layer and does not extend to the open proximal portion of the extraction bag. In embodiments, the extraction bag may possess an indicator, such as a stripe or some similar pattern, which may be colored, to identify for the clinician the location of the proximal portion of the metal cut resistant layer. In this way, the clinician desiring to break up tissue contained within the extraction bag of the present disclosure, prior to removal of the extraction bag from the body, can identify the portion of the extraction bag having the additional reinforcement by virtue of the presence of the metal cut resistant layer.

Methods for attaching the metal cut resistant layer to the inner, permeable cut resistant layer and/or outer impermeable layer include adhesive bonding, welding, heat laminating, heat-sealing, stitching, combinations thereof, and the like.

The combined layers may then be used to form an extraction bag of the present disclosure. Methods for forming extraction bags from sheets of material are within the purview of those skilled in the art. For example, in embodiments, a sheet including the combined inner cut resistant layer and outer impermeable layer, along with any optional low friction layer and/or metal cut resistant layer, may be folded upon itself so that the inner, permeable cut resistant layer forms the inner cavity of the body of the extraction bag, and the outer impermeable layer forms the outer surface of the body of the extraction bag. The edges of the layers may be sealed or sewn together to form a fluid-tight seal at the periphery of the body of the extraction bag, leaving an open end at the proximal portion of the extraction bag. In other embodiments, two sheets of the combined layers may be formed, including the inner, permeable cut resistant layer and outer impermeable layer, along with any optional low friction layer and/or metal cut resistant layer, and then one sheet placed on the other so that the inner, permeable cut resistant layers are adjacent each other. The two sheets may then be joined at the periphery to form a bag, with an open end at the proximal portion of the extraction bag as described above, so that the inner, permeable cut resistant layer defines the inner cavity of the body of the extraction bag, and the outer impermeable layer defines the outer surface of the body of the extraction bag.

Methods for forming extraction bags from sheets of materials including the inner, permeable cut resistant layer and outer impermeable layer, along with any optional low friction layer and/or metal cut resistant layer, include adhesive bonding, welding, heat-sealing, combinations thereof, and the like.

In embodiments, extraction bags of the present disclosure can be closed by pulling drawstrings positioned about the open end of the bag. In embodiments, a proximal portion of the inner, permeable cut resistant layer may project out of the open end of the extraction bag, beyond the outer impermeable layer, and then be folded over the outer impermeable layer and affixed to an outer surface of the outer impermeable layer of the extraction bag at a proximal portion of the outer impermeable layer. In this way, a cuff is formed about the open end of the bag that defines a space or channel. This space or channel defined within the cuff, in embodiments, may house drawstrings capable of closing the extraction bag in use.

Embodiments of the present disclosure will now be described in detail with reference to the drawings, in which like reference numerals designate identical or corresponding elements in each of the several views. In the following description, well-known functions or constructions are not described in detail to avoid obscuring the present disclosure in unnecessary detail.

FIG. 1 shows an extraction bag 10, according to embodiments, having a mouth portion 20 defining an opening 20a for receiving tissue and a body 30 defining an interior in communication with the opening 20a. The body 30 is liquid-tight along its edges 40.

Figure 2:
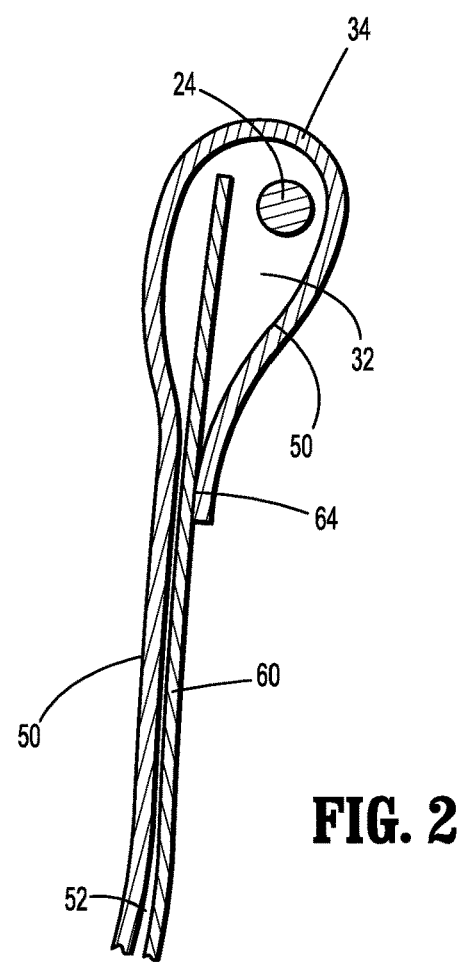
FIG. 2 is a cross-sectional view taken along section line 2-2 of FIG. 1.

As seen in FIGS. 1 and 2, the extraction bag 10 can have a closure device for closing (or substantially closing) the mouth portion 20 to further reduce the chance of a contained tissue spilling from the extraction bag 10. As shown in these drawings, the closure device can include a drawstring 24 that extends through a channel 32 (FIG. 2) defined by a cuff 34 positioned about the mouth portion 20 of the extraction bag 10. The drawstring 24 can be withdrawn from the cuff 24 to close the mouth portion 20 of the extraction bag 10 after tissue has been deposited within the body 30. As shown in FIG. 2, the body 30 is formed from inner, permeable cut resistant layer 50 and outer impermeable layer 60. The inner, permeable cut resistant layer 50 and outer impermeable layer 60 are connected at the proximal portion of the extraction bag 10 as described below. The layers 50 and 60 define a fluid collection space 52 (FIG. 2) therebetween.

As shown in FIG. 2, the proximal portion of inner, permeable cut resistant layer 50 may extend beyond and folded over the proximal portion of the outer impermeable layer 60 for attachment to external surface 64 of outer impermeable layer 60 to form the cuff 34 and define the channel 70 through which drawstring 24 can reside. Methods for attaching the proximal portion of the inner, permeable cut resistant layer 50 to the external surface of the outer impermeable layer 60 include adhesive bonding, welding, heat-sealing, stitching, combinations thereof, and the like.

In use, extraction bag 10 is introduced into the abdominal cavity, in embodiments through a trocar tube, catheter, cannula, or similar device, and is opened in the abdominal cavity where the tissue to be removed is placed in the bag.

In embodiments, the mouth of the extraction bag can have an elastomeric wire or a shape memory wire (not shown) to help hold the mouth of the extraction bag open while inside the body for the introduction of tissue therein.

Once tissue is placed within tissue extraction bag 10, the mouth portion 20 of the extraction bag 10 may be closed by pulling ends 24a and 24b of the drawstring 24 in the direction indicated by arrow "A" in FIG. 1, to minimize tissue/fluid spilling into the body of the patient.

Once the mouth portion 20 of the extraction bag 10 is closed, the extraction bag 10 can be removed from the patient's body. After the extraction bag 10 is removed, the tissue can be removed from the extraction bag 10 for further examination or the extraction bag 10 can be discarded.

An alternate embodiment of the extraction bag of the present disclosure is depicted in FIGS. 3-5. FIG. 3 depicts extraction bag 110 positioned in body cavity "C" of a patient, having tissue "T" therein. As shown in FIG. 5, the body 130 of extraction bag 110 is formed from inner, permeable cut resistant layer 150, metal cut resistant layer 180, and outer impermeable layer 160, which lie flat on one another. As depicted in FIGS. 4 and 5, metal cut resistant layer 180 does not extend to proximal portion 112 of extraction bag 110. Rather, the proximal portion 182 of metal cut resistant layer 180 terminates at a portion 132 of body 130 spaced from the mouth portion 120. Body 130 possesses indicator 136, which can be a stripe or some pattern, optionally colored, as a visual indicator to the clinician of the location of the proximal portion 182 of metal cut resistant layer 180. In this way, the clinician, should they wish to avoid introducing a morcellator or other device into any portion of the extraction bag not possessing the additional metal cut resistant layer, can visually determine where the metal cut resistant layer 180 is not present.

As shown in FIG. 4, proximal portion of inner, permeable cut resistant layer 150 may extend beyond the proximal portion of outer impermeable layer 160 and folded over the outer impermeable layer for attachment to external surface 164 of outer impermeable layer 160 to form a cuff 134 that defines a channel 132. As discussed above, the channel 170 receives a drawstring (not shown) that can be withdrawn from the cuff 134 to close the mouth portion 120 of the extraction bag 110. Methods for attaching the proximal portion of the inner, permeable cut resistant layer 150 to the external surface of the outer impermeable layer 160 include adhesive bonding, welding, heat-sealing, stitching, combinations thereof, and the like.

In embodiments, a method for retrieving tissue from the body includes forming an incision in the body, inserting a trocar tube, catheter, cannula, access port, or similar device into the incision to access a body cavity, and providing a tissue extraction bag. The method includes advancing the extraction bag through the trocar tube, catheter, cannula, access port, or similar device, and into the body cavity, placing tissue into the extraction bag while it is in the body cavity, and removing the extraction bag from the body cavity.

Where the tissue in the extraction bag is too large to be removed through the incision, the method of the present disclosure includes removing an open end of the extraction bag from the body cavity through the incision, either directly or through a cannula and/or an access port, such that a portion of the extraction bag body containing the tissue remains in the body cavity, inserting a surgical instrument (not shown) into the extraction bag, breaking up the tissue contained in the extraction bag into smaller pieces using the surgical instrument, and removing some or all of the tissue within the extraction bag to facilitate removal of the extraction bag from the body cavity. In addition, any fluid collected in the fluid collection space 52 between the inner, permeable cut resistant layer 50 and the outer impermeable layer 60 can be removed from the collection space 52 using a vacuum or the like. For example, a morcellator can be inserted into the extraction bag for morcellating the tissue. As used herein, the term morcellator refers to a surgical instrument for cutting, mincing up, liquefying, or morcellating, tissue into smaller pieces. Other devices, such as scissors, surgical knives, and the like, may be used to break up the tissue into smaller pieces. Whatever method used, care should be taken not to damage the extraction bag to prevent resected tissue from entering into the abdominal cavity.

Morcellators may be powered or hand-operated, and are generally configured to extract the tissue from the specimen bag, via, e.g., a vacuum tube or through the operation of the cutting mechanism, as the tissue is morcellated. Once a sufficient amount of morcellated tissue is removed from the extraction bag to facilitate removal of the bag from the incision, the extraction bag is then withdrawn from the patient through the incision, either directly or through the cannula and/or the access port. More specifically, if the tissue is broken down to a sufficiently small volume within the extraction bag, the extraction bag is closed with the aid of the drawstring, and the extraction bag (possessing the tissue) is removed from the body through the incision, any trocar tube, catheter, cannula, access port, or similar device, systems or instruments used during minimally invasive surgery.

The extraction bags of the present disclosure provide safe tissue extraction at the end of minimally invasive surgical procedures. Diseased tissue may be removed from the body without seeding of spilled tissue cells inside the abdomen. The design of the extraction bags of the present disclosure, possessing at least the inner, permeable cut resistant layer and, in embodiments the optional metal cut resistant layer, allows for the use of morcellators or other mechanical devices to break up tissue without tearing the extraction bag and possibly releasing tissue contents back into the body of the patient. The presently disclosed embodiments of the extraction bags also provide a cavity between layers of the extraction bag for collecting fluids from tissue collected in the extraction bag. It is further envisioned that the methods of using the extraction bags of the present disclosure may be modified to accommodate needs of a given procedure and/or the preferences of the surgeon. It is further envisioned that the embodiments disclosed herein may be used to remove any tissue or object from the body.

It will be understood that various modifications may be made to the embodiments disclosed herein. For example, other methods for introducing extraction bags of the present disclosure into the body of a patient may be used. Additionally, other extraction bag shapes may be used. Further, the terminology of similar components with the various embodiments should not be construed as specific to any particular embodiment. Thus, the above description should not be construed as limiting, but merely as exemplifications of preferred embodiments. Those skilled in the art will envision other modifications within the scope and spirit of the claims appended hereto.

What is claimed is:

1. An extraction bag for collecting tissue comprising:
a body defining a cavity and having an open end in communication with the cavity, the body formed of an inner, permeable cut resistant layer defining the cavity and an outer impermeable layer, at least a portion of a peripheral border of the inner, permeable cut resistant layer affixed to at least a portion of a peripheral border of the outer impermeable layer, thereby forming a fluid collection space between the inner, permeable cut resistant layer and the outer impermeable layer and,
a metal cut resistant layer between the inner, permeable cut resistant layer and the outer impermeable layer, wherein the metal cut resistant layer has an end spaced from the open end of the body and the extraction bag has an indicator designating the end of the metal cut resistant layer.

2. The extraction bag of claim 1, wherein the inner, permeable cut resistant layer is formed of a material selected from the group consisting of liquid crystal polymer fibers, para-aramid fibers, ultrahigh molecular weight polyethylene fibers, polytetrafluoroethylene fibers, polyurethanes, polyethylenes, block copolyetheramides, polymers of p-phenylene-2,6-benzobisoxazole, and combinations thereof.

3. The extraction bag of claim 1, wherein the outer impermeable layer is formed of a material selected from the group consisting of polyethylene, polyurethanes, polyesters, polyethylene terephthalate, thermoplastic elastomers, thermoplastic vulcanizates, silicones, natural rubbers, styrene-butadiene-styrene block copolymers, and combinations thereof.

4. The extraction bag of claim 1, wherein the peripheral border of the inner, permeable cut resistant layer is affixed to the peripheral border of the outer impermeable layer by adhesive bonding, welding, heat laminating, heat-sealing, stitching, or combinations thereof.

5. The extraction bag of claim 1, further comprising a cuff encompassing the open end, the cuff formed by folding a proximal portion of the inner, permeable cut resistant layer over a proximal portion of the outer impermeable layer and affixing the proximal portion of the inner, permeable cut resistant layer to an outer surface of the proximal portion of the outer impermeable layer of the body, thereby forming a channel within the cuff.

6. The extraction bag of claim 5, further comprising a drawstring within the channel.

7. The extraction bag of claim 1, further comprising a low friction layer on an inner surface of the inner, permeable cut resistant layer.

8. The extraction bag of claim 7, wherein the low friction layer includes a material selected from the group consisting of silicones, fluoropolymers and copolymers thereof, and combinations thereof.

9. The extraction bag of claim 1, wherein the metal cut resistant layer is formed of a material selected from the group consisting of stainless steel wires, tungsten, steel fiber yarns, and combinations thereof.

10. An extraction bag for collecting tissue comprising:
a body defining a cavity and having an open end in communication with the cavity, the body formed of an inner, permeable cut resistant layer defining the cavity, an outer impermeable layer, and a metal cut resistant layer between the inner, permeable cut resistant layer and the outer impermeable layer,
wherein the metal cut resistant layer has an end spaced from the open end of the body and the extraction bag has an indicator designating the end of the metal cut resistant layer.

11. The extraction bag of claim 10, wherein the inner, permeable cut resistant layer is formed of a material selected from the group consisting of liquid crystal polymer fibers, para-aramid fibers, ultrahigh molecular weight polyethylene fibers, polytetrafluoroethylene fibers, polyurethanes, polyethylenes, block copolyetheramides, polymers of p-phenylene-2,6-benzobisoxazole, and combinations thereof.

12. The extraction bag of claim 10, wherein the outer impermeable layer is formed of a material selected from the group consisting of polyethylene, polyurethanes, polyesters, polyethylene terephthalate, thermoplastic elastomers, thermoplastic vulcanizates, silicones, natural rubbers, styrene-butadiene-styrene block copolymers, and combinations thereof.

13. The extraction bag of claim 10, wherein the metal cut resistant layer is formed of a material selected from the group consisting of stainless steel wires, tungsten, steel fiber yarns, and combinations thereof.

14. The extraction bag of claim 10, further comprising a cuff encompassing the open end, the cuff formed by folding a proximal portion of the inner, permeable cut resistant layer over a proximal portion of the outer impermeable layer and affixing the proximal portion of the inner, permeable cut resistant layer to an outer surface of the proximal portion of the outer impermeable layer of the body, thereby forming a channel within the cuff.

15. The extraction bag of claim 14, further comprising a drawstring within the channel.

16. The extraction bag of claim 10, further comprising a low friction layer on an inner surface of the inner, permeable cut resistant layer.

17. The extraction bag of claim 16, wherein the low friction layer includes a material selected from the group consisting of silicones, fluoropolymers and copolymers thereof, and combinations thereof.

* * * * *